(12) United States Patent
Khunt et al.

(10) Patent No.: US 7,947,699 B2
(45) Date of Patent: May 24, 2011

(54) ANHYDROUS AMORPHOUS IMATINIB MESYLATE

(75) Inventors: Mayur Devjibhai Khunt, Gujarat (IN); Nilesh Sudhir Patil, Maharashtra (IN); Haushabhau Shivaji Pagire, Maharashtra (IN); Nitin Sharadchandra Pradhan, Maharashtra (IN); Jon Valgeirsson, Hafnarfjordur (IE)

(73) Assignee: Actavis Group PTC EHF (IS)

( * ) Notice: Subject to any disclaimer, the term of this patent is extended or adjusted under 35 U.S.C. 154(b) by 75 days.

(21) Appl. No.: 12/350,995

(22) Filed: Jan. 9, 2009

(65) Prior Publication Data

US 2009/0181977 A1    Jul. 16, 2009

(30) Foreign Application Priority Data

Jan. 10, 2008   (IN) .............................. 100/CHE/2008

(51) Int. Cl.
*A61K 31/505*   (2006.01)
(52) U.S. Cl. ........ 514/275; 424/464; 544/331; 544/364; 546/268.1
(58) Field of Classification Search .................. 424/464; 514/275; 544/331, 364; 546/268.1
See application file for complete search history.

(56) References Cited

U.S. PATENT DOCUMENTS

| 5,521,184 A | 5/1996 | Zimmermann |
| 7,300,938 B2 | 11/2007 | Parthasaradhi et al. |

FOREIGN PATENT DOCUMENTS

| WO | 2005077933 A1 | 8/2005 |
| WO | 2005095379 A2 | 10/2005 |
| WO | 2006024863 A1 | 3/2006 |
| WO | 2006048890 A1 | 5/2006 |
| WO | 2006054314 A1 | 5/2006 |
| WO | 2007023182 A1 | 3/2007 |
| WO | 2007136510 A2 | 11/2007 |
| WO | WO 2007/136510 | * 11/2007 |

OTHER PUBLICATIONS

Konno, Tsutomu; "Physical and Chemical Changes of Medicinals in Mixtures with Adsorbents in the Solid State. IV. Study on Reduced-Pressure Mixing for Practical Use of Amorphous Mixtures of Flufenamic Acid"; Chem. Pharm. Bull.; 38; pp. 2003-2007; (1990).

* cited by examiner

*Primary Examiner* — James O Wilson
*Assistant Examiner* — Douglas M Willis
(74) *Attorney, Agent, or Firm* — Cantor Colburn LLP

(57) ABSTRACT

Described is a highly stable amorphous form of imatinib mesylate having a water content of less than 0.5 percent by weight, based on the total weight of the amorphous imatinib mesylate, (anhydrous amorphous imatinib mesylate), a process for preparation thereof, and pharmaceutical compositions.

20 Claims, 1 Drawing Sheet

Powder X-Ray diffraction (XRD) pattern of Amorphous Imatinib Mesylate having a water content of less than 0.5 percent.

ANHYDROUS AMORPHOUS IMATINIB MESYLATE

CROSS REFERENCE TO RELATED APPLICATION

This application claims the benefit of priority to Indian provisional application No. 100/CHE/2008, filed on Jan. 10, 2008, which is incorporated herein by reference.

FIELD OF THE DISCLOSURE

The present invention relates to a stable amorphous form of imatinib mesylate, a process for the preparation thereof, and pharmaceutical compositions comprising amorphous imatinib mesylate.

BACKGROUND

U.S. Pat. No. 5,521,184 discloses a variety of N-phenyl-2-pyrimidine-amine derivatives, processes for their preparation, pharmaceutical compositions and methods of use thereof. These compounds are useful in the treatment of tumoral diseases. Among them, imatinib, 4-[(4-methyl-1-piperazinyl)methyl]-N-[4-methyl-3-[[4-(3-pyridinyl)-2-pyrimidinyl]amino]phenyl]benzamide, is a protein-tyrosine kinase inhibitor, especially useful in the treatment of various types of cancer and for the treatment of atherosclerosis, thrombosis, restenosis, or fibrosis. Thus, imatinib can be used for the treatment of non-maligant diseases. Imatinib is usually administered orally in the form of a suitable salt, e.g., in the form of imatinib mesylate. Imatinib mesylate is represented by the following structural formula:

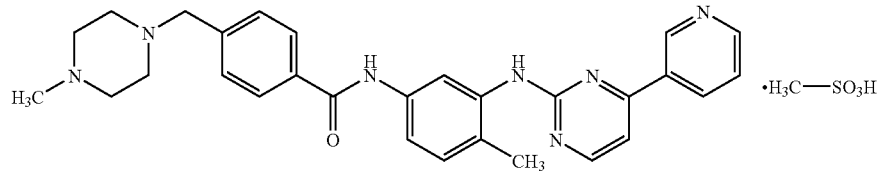

Imatinib is sold by Novartis under the brand name Gleevec™ or Glivec® in the form of capsules containing imatinib mesylate equivalent to 100 mg of imatinib free base.

Imatinib mesylate can exist in different polymorphic forms, which differ from each other in terms of stability, physical properties, spectral data and methods of preparation. Various polymorphic forms, including hydrated and solvated forms, of imatinib mesylate designated Forms α, β, H1, α2, δ, ε, I, II, F, G, H, I, K, IV, V, VI, VII, VIII, IX, X, XI, XIII, XIV, XV, XVI and amorphous forms are apparently disclosed in U.S. Pat. No. 6,894,051 B1, U.S. Pat. No. 7,300,938 B2, PCT Patent Publication Nos. WO 2005/077933, WO 2005/095379, WO 2006/054314, WO 2006/024863, WO 2006/048890, WO 2007/023182, and WO 2007/136510.

U.S. Pat. No. 6,894,051 B1 (hereinafter referred to as the '051 patent) discloses two crystalline modifications (α-form and β-form) of imatinib mesylate. The '051 patent mentioned amorphous imatinib mesylate. However, the processes are not described for preparation of amorphous imatinib mesylate.

U.S. Pat. No. 7,300,938 B2 (hereinafter referred to as the '938 patent) discloses a crystalline (Form H1) and an amorphous hydrate (water content: 2.0-3.2 percent w/w) form of imatinib mesylate, and processes for their preparations thereof.

The pending Indian Patent Application No. 1209/MUM/2003 (hereinafter referred to as the '1209 patent application) teaches an amorphous form of imatinib mesylate having a water content of 1.5-5 percent w/w (γ-form), and a process for preparing it.

The hydrated amorphous form of imatinib mesylate disclosed in the '938 patent and the '1209 patent applications is often not very stable, hygroscopic in nature, and not ideal for the preparation of pharmaceutical composition.

PCT Publication No. 2007/136510 describes two processes for the preparation of the amorphous form of imatinib mesylate. According to the first process, amorphous imatinib mesylate is prepared by providing a solution of imatinib mesylate in a solvent selected from the group consisting of methanol, methoxyethanol, ethoxyethanol, N-methylpyrrolidone, propylene carbonate, acetonitrile, nitromethane, pyridine, dimethylsulfoxide, and mixtures thereof, and admixing the solution with an anti-solvent selected from the group consisting of ethyl acetate, butyl acetate, diethyl ether, tert-butyl methyl ether, tetrahydrofuran, dioxane, methylal, ethylal and 1,3-dioxolane to obtain a precipitate of the amorphous form. According to the second process, amorphous imatinib mesylate is prepared by providing a solution of imatinib mesylate in a solvent selected from the group consisting of isobutanol, n-butanol, methoxy ethanol or ethoxyethanol, N-methylpyrrolidone, acetic acid, propylene carbonate, acetonitrile, nitromethane, pyridine, dimethylsulfoxide, and mixture thereof, and cooling the solution to a temperature of about 30° C. to about −50° C. to obtain the amorphous imatinib mesylate.

The processes for preparation of amorphous imatinib mesylate as described in the PCT Publication No. 2007/136510 A2 (hereinafter referred to as the '510 application) fail to consistently produce the amorphous imatinib mesylate. The amorphous form of imatinib mesylate obtained by the processes described in the '510 application has a water content of greater than about 1 percent w/w, does not have satisfactory purity. The amorphous imatinib mesylate is often not very stable, hygroscopic in nature, and not ideal for the preparation of pharmaceutical composition.

It has been previously disclosed that the amorphous forms in a number of drugs exhibit superior dissolution characteristics and in some cases different bioavailability patterns compared to crystalline forms [Konne T., Chem. Pharm. Bull., 38, 2003 (1990)]. For some therapeutic indications, one bioavailability pattern may be favored over another. An amorphous form of cefuroxime axetil is good example of a form exhibiting higher bioavailability than the crystalline forms.

Therefore, there is a need for a highly stable anhydrous amorphous imatinib mesylate, a process for preparing it, and a pharmaceutical composition comprising it.

SUMMARY

In one aspect, described herein is a highly stable amorphous form of imatinib mesylate having a water content of less than 0.5 percent by weight based on the total weight of the amorphous imatinib mesylate (i.e., anhydrous amorphous imatinib mesylate).

In another aspect, encompassed herein is a process for preparing the highly stable amorphous imatinib mesylate having a water content of less than 0.5 percent by weight based on the total weight of the amorphous imatinib mesylate.

In an embodiment, the amorphous imatinib mesylate has a water content of less than about 0.4 percent by weight, specifically less than about 0.2 percent by weight, and more specifically less than about 0.1 percent by weight, and still more specifically is essentially free from water, based on the total weight of the amorphous imatinib mesylate.

In another aspect, provided herein is a pharmaceutical composition comprising amorphous imatinib mesylate having a water content of less than 0.5 percent by weight, based on the total weight of the amorphous imatinib mesylate, and one or more pharmaceutically acceptable excipients.

In still another aspect, provided herein is a pharmaceutical composition comprising amorphous imatinib mesylate having water content less than 0.5 percent by weight, based on the total weight of the amorphous imatinib mesylate, made by the process disclosed herein, and one or more pharmaceutically acceptable excipients.

In still further aspect, encompassed herein is a process for preparing a pharmaceutical formulation comprising combining amorphous imatinib mesylate having a water content of less than 0.5 percent by weight, based on the total weight of the amorphous imatinib mesylate, with one or more pharmaceutically acceptable excipients.

DETAILED DESCRIPTION

Figure 1:
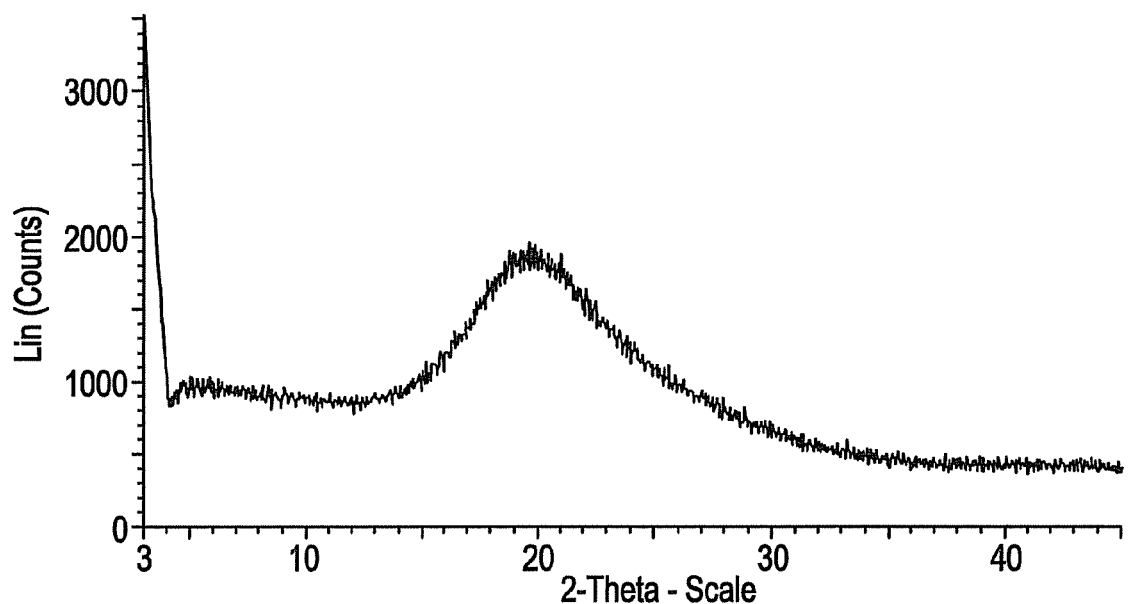
FIG. 1 a characteristic powder X-ray diffraction (XRD) pattern of amorphous imatinib mesylate having a water content of less than 0.5 percent.

It has been unexpectedly found that a uniformly amorphous form of imatinib mesylate having a water content of less than 0.5 percent by weight, based on the total weight of the amorphous imatinib mesylate, can be obtained in a simple and reproducible process.

Extensive laboratory and full-scale research has resulted in a new and inventive process for producing a highly stable and substantially pure amorphous form of imatinib mesylate having water content less than 0.5 percent by weight, based on the total weight of the amorphous imatinib mesylate. The amorphous imatinib mesylate having water content less than 0.5 percent by weight, based on the total weight of the amorphous imatinib mesylate, can be utilized to prepare stable pharmaceutical dosage forms having good dissolution properties.

According to one aspect, there is provided a stable and substantially pure amorphous form of imatinib mesylate having water content less than 0.5 percent by weight, based on the total weight of the amorphous imatinib mesylate (anhydrous amorphous imatinib mesylate).

The amorphous form of imatinib mesylate having water content less than 0.5 percent by weight, based on the total weight of the amorphous imatinib mesylate, is characterized by a powder XRD pattern substantially in accordance with FIG. 1. The X-ray powder diffraction pattern shows no peaks, thus demonstrating the amorphous nature of the product.

According to another aspect, a process is provided for the preparation of amorphous imatinib mesylate having water content less than 0.5 percent by weight, based on the total weight of the amorphous imatinib mesylate, comprising:

a) forming a first solution of imatinib mesylate in an anhydrous solvent medium comprising a first organic solvent and a second organic solvent, wherein the first organic solvent is a $C_1$ to $C_4$ straight or branched chain alcohol, a chlorinated hydrocarbon, or a mixture thereof, and wherein the second organic solvent is an aromatic hydrocarbon solvent;

b) heating the first solution obtained in step-(a) under azeotropic conditions at a temperature of about 35° C. to about 110° C. to form a heated first solution;

c) substantially removing the first organic solvent from the heated first solution azeotropically at a temperature of about 35° C. to about 110° C. to form a reaction mass;

d) heating the reaction mass obtained in step-(c) azeotropically at a temperature of about 110° C. to about 150° C. to form a heated reaction mass;

e) substantially removing the remaining organic solvent from the heated reaction mass at a temperature of about 110° C. to about 150° C., optionally under azeotropic conditions, to provide a residue containing imatinib mesylate having water content less than about 0.5 percent by weight, based on the total weight of the imatinib mesylate;

f) dissolving the residue obtained in step-(e) in a third organic solvent such as a $C_1$ to $C_4$ straight or branched chain alcohol, a chlorinated hydrocarbon solvent, or a mixture thereof to provide a second solution; and g) substantially removing the third organic solvent from the second solution obtained in step-(f) to provide the amorphous imatinib mesylate having water content less than 0.5 percent by weight, based on the total weight of the amorphous imatinib mesylate.

The term "substantially removing" the solvent or solvent mixture refers to at least 10%, specifically greater than about 50%, more specifically greater than about 90%, still more specifically greater than about 99%, and most specifically essentially complete, removal of the defined solvent or solvent mixture from the solvent solution or the reaction mass containing the solvent or solvent mixture.

The process can produce amorphous form of imatinib mesylate in substantially pure form.

The term "substantially pure amorphous imatinib mesylate" refers to the amorphous imatinib mesylate having purity greater than about 99%, specifically greater than about 99.5%, more specifically greater than about 99.8% and still more specifically greater than about 99.9% (measured by HPLC).

In a preferred embodiment, the amorphous imatinib mesylate has a water content of less than about 0.4 percent by weight, specifically less than about 0.2 percent by weight, and more specifically less than about 0.1 percent by weight, and still more specifically is essentially free from water, based on the total weight of the amorphous imatinib mesylate.

The amorphous imatinib mesylate having water content less than 0.5 percent by weight obtained by the process disclosed herein is stable, consistently reproducible and has good flow properties, and which is particularly suitable for bulk preparation and handling, and so, the amorphous imatinib mesylate having water content less than 0.5 percent by weight obtained by the process disclosed herein is suitable for formulating imatinib mesylate.

Exemplary aromatic hydrocarbon solvents include, but are not limited to, toluene, xylene, and mixtures thereof. A specific aromatic hydrocarbon solvent is toluene. Exemplary $C_1$ to $C_4$ straight or branched chain alcohol solvents include, but are not limited to, methanol, ethanol, n-propanol, isopropanol, tert-butanol, n-butanol, and mixtures thereof. A specific alcoholic solvent is methanol. Exemplary chlorinated hydrocarbon solvents include, but are not limited to, methylene chloride, ethyl dichloride, chloroform, carbontetrachloride, and mixtures thereof. Specific chlorinated hydrocarbon solvents are methylene chloride and chloroform.

In one embodiment, the first organic solvent used in step-(a) is selected from the group consisting of methanol, ethanol, isopropanol, methylene chloride, chloroform, and mixtures thereof. In another embodiment, the first organic solvent used in step-(a) is selected from the group consisting of methanol, chloroform, and mixtures thereof. Specifically, the second organic solvent is toluene.

Step-(a) of forming a solution of imatinib mesylate includes dissolving any form of imatinib mesylate in the anhydrous solvent medium, or obtaining an existing solution from a previous processing step.

In one embodiment, the imatinib mesylate is dissolved in the anhydrous solvent medium at a temperature of below about reflux temperature of the solvent medium used, more specifically at about 20° C. to about 110° C., and still more specifically at about 40° C. to about 80° C.

As used herein, "reflux temperature" means the temperature at which the solvent or solvent system refluxes or boils at atmospheric pressure.

The solution in step-(a) may also be prepared by admixing imatinib base, methanesulfonic acid and the solvent medium to obtain a mixture; and heating the mixture to obtain a solution of imatinib mesylate. In one embodiment, the mixture is heated at a temperature of about 40° C. to about 110° C., and more preferably at about 50° C. to about 80° C.

The solution obtained in step-(a) or step-(f) is optionally subjected to carbon treatment. The carbon treatment is carried out by methods known in the art, for example by stirring the solution with finely powdered carbon at a temperature of below about 70° C. for at least 15 minutes, specifically at a temperature of about 40° C. to about 70° C. for at least 30 minutes; and filtering the resulting mixture through hyflo to obtain a filtrate containing imatinib mesylate by removing charcoal. In one embodiment, finely powdered carbon is an active carbon.

The heating in step-(b) is carried out at a temperature of about 60° C. to about 110° C. for at least 15 minutes, specifically at about 80° C. to about 110° C. from about 20 minutes to about 5 hours, and most specifically at about 100° C. to about 110° C. from about 30 minutes to about 2 hours.

Removal of solvent in step-(c) is accomplished by azeotropic distillation of the first organic solvent from the solution under inert atmosphere to ensure the elimination of moisture present in the solution.

The distillation process can be performed at atmospheric pressure or reduced pressure. Specifically, the distillation is carried out at a temperature of about 60° C. to about 110° C., more specifically at about 80° C. to about 110° C., and most specifically at about 100° C. to about 110° C.

In one embodiment, the solvent is removed at a pressure of about 760 mm Hg or less, more specifically at about 400 mm Hg or less, still more specifically at about 80 mm Hg or less, and most specifically from about 30 to about 80 mm Hg.

The heating in step-(d) is carried out at a temperature of about 110° C. to about 140° C. for at least 15 minutes, specifically at about 110° C. to about 130° C. from about 30 minutes to about 5 hours, and most specifically at about 110° C. to about 120° C. from about 1 hour to about 3 hours.

Removal of solvent in step-(e) is accomplished, for example, by substantially complete evaporation of the solvent, concentrating the solution or distillation of solvent, under inert atmosphere to substantial elimination of moisture along with the total organic solvent present in the reaction mass.

The distillation process can be performed at atmospheric pressure or reduced pressure. Specifically, the distillation is carried out at a temperature of about 110° C. to about 140° C., more specifically at about 110° C. to about 130° C., and most specifically at about 110° C. to about 120° C.

Specifically, the solvent is removed at a pressure of about 760 mm Hg or less, more specifically at about 400 mm Hg or less, still more specifically at about 80 mm Hg or less, and most specifically from about 30 to about 80 mm Hg.

The residue containing imatinib mesylate having water content less than about 0.5 percent by weight in step-(f) is dissolved in the organic solvent at a temperature of below about reflux temperature of the solvent used, specifically at about 40° C. to about 60° C., and more specifically at about 45° C. to about 55° C.

Specifically, the organic solvent used in step-(f) is selected from the group consisting of methanol, ethanol, isopropanol, methylene chloride, chloroform, and mixtures thereof, more specifically selected from the group consisting of methanol, chloroform, and mixtures thereof, and most specifically methanol.

Removal of solvent in Step-(g) is accomplished, for example, by substantially complete evaporation of the solvent, concentrating the solution or distillation of solvent, under inert atmosphere to obtain amorphous imatinib mesylate having water content less than 0.5 percent by weight.

The distillation process can be performed at atmospheric pressure or reduced pressure. Specifically the solvent is removed at a pressure of about 760 mm Hg or less, more specifically at about 400 mm Hg or less, still more specifically at about 80 mm Hg or less, and most specifically from about 30 to about 80 mm Hg.

The solution may also be completely evaporated in, for example, a pilot plant Rota vapor, a Vacuum Paddle Dryer or in a conventional reactor under vacuum above about 720 mm Hg by flash evaporation techniques by using an agitated thin film dryer ("ATFD"), or evaporated by spray drying to obtain a dry amorphous powder.

Solvents can also be removed by spray-drying, in which a solution of imatinib mesylate is sprayed into the spray drier at the flow rate ranging from 10 to 300 ml/hr, preferably flow rate is 40 to 200 ml/hr. The air inlet temperature to the spray drier used may range from about 30° C. to about 150° C., specifically from about 65° C. to about 110° C. and the outlet air temperature used may range from about 30° C. to about 90° C.

Another suitable method is vertical agitated thin-film drying (or evaporation). Agitated thin film evaporation technology involves separating the volatile component using indirect heat transfer coupled with mechanical agitation of the flowing film under controlled condition. In vertical agitated thin-film drying (or evaporation) (ATFD-V), the starting solution is fed from the top into a cylindrical space between a centered rotary agitator and an outside heating jacket. The rotor rotation agitates the downside-flowing solution while the heating jacket heats it.

The pure amorphous imatinib mesylate obtained by above process may be further dried in, for example, Vacuum Tray Dryer, Rotocon Vacuum Dryer, Vacuum Paddle Dryer or pilot plant Rota vapor, to further lower residual solvents. Drying can be carried out under reduced pressure until the residual solvent content reduces to the desired amount such as an amount that is within the limits given by the International Conference on Harmonization of Technical Requirements for Registration of Pharmaceuticals for Human Use ("ICH") guidelines.

In an embodiment, the drying is carried out at atmospheric pressure or reduced pressures, such as below about 200 mm Hg, or below about 50 mm Hg, at temperatures such as about 35° C. to about 70° C. The drying can be carried out for any desired time period that achieves the desired result, such as times about 1 to 20 hours. Drying may also be carried out for shorter or longer periods of time depending on the product specifications. Temperatures and pressures will be chosen based on the volatility of the solvent being used and the foregoing should be considered as only a general guidance. Drying can be suitably carried out in a tray dryer, vacuum oven, air oven, or using a fluidized bed drier, spin flash dryer, flash dryer and the like. Drying equipment selection is well within the ordinary skill in the art.

Imatinib free base and imatinib mesylate used as starting materials in the above process may be obtained by processes described in the prior art, for example by the processes described in the U.S. Pat. No. 5,521,184.

The purity of the amorphous imatinib mesylate obtained by the process disclosed herein is of greater than about 99%, specifically greater than about 99.5%, more specifically greater than about 99.9%, and most specifically greater than about 99.95% as measured by HPLC. For example, the purity of the amorphous imatinib mesylate of the present invention can be about 99% to about 99.95%, or about 99.5% to about 99.99%.

Further encompassed herein is the use of amorphous imatinib mesylate having a water content of less than 0.5 percent by weight, based on the total weight of the amorphous imatinib mesylate, for the manufacture of a pharmaceutical composition.

A specific pharmaceutical composition of amorphous imatinib mesylate having a water content of less than 0.5 percent by weight, based on the total weight of the amorphous imatinib mesylate, is selected from a solid dosage form and an oral suspension.

In one embodiment, the amorphous imatinib mesylate having a water content of less than 0.5 percent by weight of the present invention has a $D_{50}$ and/or $D_{90}$ particle size of less than or equal to about 400 microns, specifically less than or equal to about 200 microns, more specifically less than or equal to about 150 microns, still more specifically less than or equal to about 50 microns, and most specifically less than or equal to about 15 microns.

In another embodiment, the substantially pure amorphous imatinib mesylate having a water content of less than 0.5 percent by weight disclosed herein for use in the pharmaceutical compositions has a 90 volume-percent of the particles ($D_{90}$) have a size of less than or equal to about 400 microns, specifically less than or equal to about 200 microns, more specifically less than or equal to about 150 microns, still more specifically less than or equal to about 50 microns, and most specifically less than or equal to about 15 microns.

In another embodiment, the particle sizes of amorphous imatinib mesylate having a water content of less than 0.5 percent by weight can be achieved by a mechanical process of reducing the size of particles which includes any one or more of cutting, chipping, crushing, milling, grinding, micronizing, trituration or other particle size reduction methods known in the art, to bring the solid state forms the desired particle size range.

According to another aspect, there is provided pharmaceutical compositions comprising amorphous imatinib mesylate having a water content of less than 0.5 percent by weight, based on the total weight of the amorphous imatinib mesylate, prepared according to processes disclosed herein and one or more pharmaceutically acceptable excipients.

According to another aspect, there is provided a process for preparing a pharmaceutical formulation comprising combining amorphous imatinib mesylate having a water content of less than 0.5 percent by weight, based on the total weight of the amorphous imatinib mesylate, prepared according to processes disclosed herein, with one or more pharmaceutically acceptable excipients.

Yet another embodiment, disclosed herein are pharmaceutical compositions comprising at least a therapeutically effective amount of substantially pure amorphous imatinib mesylate having water content less than 0.5 percent by weight, based on the total weight of the amorphous imatinib mesylate. Such pharmaceutical compositions may be administered to a mammalian patient in any dosage form, e.g., liquid, powder, elixir, injectable solution, etc. Dosage forms may be adapted for administration to the patient by oral, buccal, parenteral, ophthalmic, rectal and transdermal routes or any other acceptable route of administration. Oral dosage forms include, but are not limited to, tablets, pills, capsules, troches, sachets, suspensions, powders, lozenges, elixirs and the like. The pure amorphous imatinib mesylate having water content less than 0.5 percent by weight may also be administered as suppositories, ophthalmic ointments and suspensions, and parenteral suspensions, which are administered by other routes.

The dosage forms may contain substantially pure amorphous imatinib mesylate having water content less than 0.5 percent by weight as is or, alternatively, may contain substantially pure amorphous imatinib mesylate having a water content of less than 0.5 percent by weight of the present invention as part of a composition. The pharmaceutical compositions may further contain one or more pharmaceutically acceptable excipients. Suitable excipients and the amounts to use may be readily determined by the formulation scientist based upon experience and consideration of standard procedures and reference works in the field, e.g., the buffering agents, sweetening agents, binders, diluents, fillers, lubricants, wetting agents and disintegrants described hereinabove.

In one embodiment, capsule dosages contain substantially pure amorphous imatinib mesylate having a water content of less than 0.5 percent by weight of the present invention within a capsule which may be coated with gelatin. Tablets and powders may also be coated with an enteric coating. The enteric-coated powder forms may have coatings containing at least phthalic acid cellulose acetate, hydroxypropylmethyl cellulose phthalate, polyvinyl alcohol phthalate, carboxy methyl ethyl cellulose, a copolymer of styrene and maleic acid, a copolymer of methacrylic acid and methyl methacrylate, and like materials, and if desired, they may be employed with suitable plasticizers and/or extending agents. A coated capsule or tablet may have a coating on the surface thereof or may be a capsule or tablet comprising a powder or granules with an enteric-coating.

Tableting compositions may have few or many components depending upon the tableting method used, the release rate desired and other factors. For example, the compositions described herein may contain diluents such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents such calcium carbonate and calcium diphosphate and other diluents known to one of ordinary skill in the art. Yet other suitable diluents include waxes, sugars (e.g. lactose) and sugar alcohols like mannitol and sorbitol, acrylate polymers and copolymers, as well as pectin, dextrin and gelatin.

Other excipients include binders, such as acacia gum, pregelatinized starch, sodium alginate, glucose and other binders used in wet and dry granulation and direct compression tableting processes; disintegrants such as sodium starch glycolate, crospovidone, low-substituted hydroxypropyl cellulose and others; lubricants like magnesium and calcium stearate and sodium stearyl fumarate; flavorings; sweeteners; preservatives; pharmaceutically acceptable dyes and glidants such as silicon dioxide.

Instrumental Details:

Water Content:

The water content was determined by using the Mettler Toledo DL-50 graphics apparatus.

Purity by HPLC:

The HPLC purity was measured by high performance liquid chromatography by using Water's HPLC system having alliance 2695 model pump and 2487 (UV) detector with Empower chromatography software or its equivalent under the following conditions:

| Column | XBridge C18, 250 × 4.6 mm × 5.0 micron |
|---|---|
| Make | Waters, part Number: 186003117 |
| Detector | UV at 230 nm |
| Injection volume | 10.0 μL |
| Run time | 40 min |
| Column temperature | 40° C. |
| Flow rate | 1.0 ml/min |
| Diluent | Mobile phase B |

Buffer preparation:

1.4 g of Di Sodium hydrogen phosphate was taken in 1000 ml of water followed by adjusting pH to 8.0 with diluted $H_3PO_4$ and then filtered through 0.22 μm or finer porosity membrane and degas.

| Mobile Phase-A | Buffer (100 percent) |
|---|---|
| Mobile Phase-B | Buffer:Methanol (30 percent:70 percent v/v) |

X-Ray Powder Diffractometer:

The X-Ray powder diffraction was measured by an X-ray powder diffractometer equipped with a Cu-anode (λ=1.54 Angstrom), X-ray source operated at 40 kV, 40 mA and a Ni filter is used to strip K-beta radiation. Two-theta calibration is performed using an NIST SRM 1976, Corundum standard. The sample was analyzed using the following instrument parameters: measuring range=3-45° 2θ; step width=0.01579°; and measuring time per step=0.11 second.

The following examples are provided to enable one skilled in the art to practice the invention and are merely illustrate the process of this invention. However, it is not intended in any way to limit the scope of the present invention.

EXAMPLES

Example 1

Toluene (400 ml) and imatinib mesylate (20 gm) were placed in a moisture free round bottom flask, the resulting suspension was heated at 50-55° C. followed by the addition of methanol (100 ml) to form a clear solution. The resulting solution was stirred for 30 to 60 minutes at reflux temperature (100-110° C.) followed by distillation of methanol with Dean-Stark apparatus. After complete distillation of methanol from the reaction mass, the resulting mass was heated at 120-125° C. under azeotropic reflux for 3 to 4 hours. Distillation of toluene was started after azeotropical maintenance to ensure the moisture elimination in the reaction mass at 120-125° C. Toluene was removed from the reaction mass completely up to maximum extent and then subjected to vacuum to remove the traces of toluene followed by the addition of methanol (150 ml) at 40-50° C. Methanol was distilled off (atmospherically) completely from the resulting solution at 80-90° C, the resulting oily residue was then subjected to high vacuum to remove the traces of methanol and then degassed for 3 hours at 80-90° C. to give 19 gm of amorphous imatinib mesylate (HPLC Purity: 99.92%; Water Content: 0.40 percent by weight).

Example 2

Imatinib mesylate (20 gm) was placed in a moisture free round bottom flask followed by the addition of methanol (200 ml) and chloroform (600 ml) at 25-30° C., and the resulting mixture was heated at 60-65° C. until to form a clear solution. This was followed by the addition of toluene (600 ml) at 60-65° C. and the resulting solution was heated to reflux (100-110° C.) using Dean-Stark apparatus for 3-4 hours. This was followed by removal of 800 ml of solvent using Dean-Stark apparatus. The resulting mass was heated at 110-120° C. and maintained for 3-4 hours followed by the removal of toluene up to maximum extent (water content was less than 0.5 percent). Methanol (500 ml) was added to the resulting residue and then distilled off methanol to get an oily residue. The oily residue was subjected to high vacuum to remove the traces of methanol and then degassed for 3 hours at 85-90° C. to give 18.7 gm of amorphous imatinib mesylate (HPLC Purity: 99.79 percent; Water Content: 0.45 percent by weight).

Example 3

Imatinib mesylate (20 gm) was placed in a moisture free round bottom flask followed by the addition of methanol (30 ml) and chloroform (700 ml) at 25-30° C., and the resulting mixture was heated at 60-65° C. until to form a clear solution. This was followed by the addition of toluene (200 ml) at 60-65° C. and the resulting solution was heated to reflux (100-110° C.) using Dean-Stark apparatus for 3-4 hours. This was followed by removal of 700 ml of solvent using Dean-Stark apparatus. The resulting mass was heated at 110-120° C. and maintained for 3-4 hours followed by removal of toluene up to maximum extent (water content is less than 0.5 percent). Methanol (60 ml) and chloroform (300 ml) were added to the reaction mass and then distilled off solvent to get an oily residue. The oily residue was subjected to high vacuum to remove the traces of solvent and then degassed for 3 hours at 85-90° C. to give 18.8 gm of amorphous imatinib mesylate (HPLC Purity: 99.84%; Water Content: 0.43 percent by weight).

Unless otherwise indicated, the following definitions are set forth to illustrate and define the meaning and scope of the various terms used to describe the invention herein.

The term "amorphous" means a solid without long-range crystalline order. Amorphous form of imatinib mesylate preferably contain less than about 10 percent crystalline forms of imatinib mesylate, more preferably less than 5 percent crystalline forms of imatinib mesylate, and still more preferably is essentially free of crystalline forms of imatinib mesylate.

"Essentially free of crystalline forms of imatinib mesylate" means that no crystalline polymorph forms of imatinib mesylate can be detected within the limits of a powder X-ray diffractometer.

The term "pharmaceutically acceptable" means that which is useful in preparing a pharmaceutical composition that is generally non-toxic and is not biologically undesirable and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

The term "therapeutically effective amount" as used herein means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The term "delivering" as used herein means providing a therapeutically effective amount of an active ingredient to a particular location within a host causing a therapeutically effective blood concentration of the active ingredient at the particular location. This can be accomplished, e.g., by topical, local or by systemic administration of the active ingredient to the host.

The term "buffering agent" as used herein is intended to mean a compound used to resist a change in pH upon dilution or addition of acid of alkali. Such compounds include, by way of example and without limitation, potassium metaphosphate, potassium phosphate, monobasic sodium acetate and sodium citrate anhydrous and dehydrate and other such material known to those of ordinary skill in the art.

The term "sweetening agent" as used herein is intended to mean a compound used to impart sweetness to a formulation. Such compounds include, by way of example and without limitation, aspartame, dextrose, glycerin, mannitol, saccharin sodium, sorbitol, sucrose, fructose and other such materials known to those of ordinary skill in the art.

The term "binders" as used herein is intended to mean substances used to cause adhesion of powder particles in granulations. Such compounds include, by way of example and without limitation, acacia alginic acid, tragacanth, carboxymethylcellulose sodium, polyvinylpyrrolidone, compressible sugar (e.g., NuTab), ethylcellulose, gelatin, liquid glucose, methylcellulose, povidone and pregelatinized starch, combinations thereof and other material known to those of ordinary skill in the art.

Exemplary binders include starch, polyethylene glycol, guar gum, polysaccharide, bentonites, sugars, invert sugars, poloxamers (PLURONIC™ F68, PLURONIC™ F127), collagen, albumin, celluloses in non-aqueous solvents, combinations thereof and the like. Other binders include, for example, polypropylene glycol, polyoxyethylene-polypropylene copolymer, polyethylene ester, polyethylene sorbitan ester, polyethylene oxide, microcrystalline cellulose, polyvinylpyrrolidone, combinations thereof and other such materials known to those of ordinary skill in the art.

The term "diluent" or "filler" as used herein is intended to mean inert substances used as fillers to create the desired bulk, flow properties, and compression characteristics in the preparation of solid dosage formulations. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

The term "glidant" as used herein is intended to mean agents used in solid dosage formulations to improve flow-properties during tablet compression and to produce an anti-caking effect. Such compounds include, by way of example and without limitation, colloidal silica, calcium silicate, magnesium silicate, silicon hydrogel, cornstarch, talc, combinations thereof and other such materials known to those of ordinary skill in the art.

The term "lubricant" as used herein is intended to mean substances used in solid dosage formulations to reduce friction during compression of the solid dosage. Such compounds include, by way of example and without limitation, calcium stearate, magnesium stearate, mineral oil, stearic acid, zinc stearate, combinations thereof and other such materials known to those of ordinary skill in the art.

The term "disintegrant" as used herein is intended to mean a compound used in solid dosage formulations to promote the disruption of the solid mass into smaller particles, which are more readily dispersed or dissolved. Exemplary disintegrants include, by way of example and without limitation, starches such as corn starch, potato starch, pregelatinized, sweeteners, clays, such as bentonite, microcrystalline cellulose (e.g. Avicel™), carsium (e.g. Amberlite™), alginates, sodium starch glycolate, gums such as agar, guar, locust bean, karaya, pectin, tragacanth, combinations thereof and other such materials known to those of ordinary skill in the art.

The term "wetting agent" as used herein is intended to mean a compound used to aid in attaining intimate contact between solid particles and liquids. Exemplary wetting agents include, by way of example and without limitation, gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters, (e.g., TWEEN™s), polyethylene glycols, polyoxyethylene stearates colloidal silicon dioxide, phosphates, sodium dodecylsulfate, carboxymethylcellulose calcium, carboxymethylcellulose sodium, methylcellulose, hydroxyethylcellulose, hydroxyl propylcellulose, hydroxypropylmethylcellulose phthalate, noncrystalline cellulose, magnesium aluminum silicate, triethanolamine, polyvinyl alcohol, and polyvinylpyrrolidone (PVP). Tyloxapol (a nonionic liquid polymer of the alkyl aryl polyether alcohol type) is another useful wetting agent, combinations thereof and other such materials known to those of ordinary skill in the art.

As used herein, $D_X$ means that X percent of the particles have a diameter less than a specified diameter D. Thus, a $D_{90}$ or d(0.9) of less than 300 microns means that 90 volume-percent of the micronized particles in a composition have a diameter less than 300 microns.

The term "micronization" used herein means a process or method by which the size of a population of particles is reduced.

As used herein, the term "micron" or "µm" refer to "micrometer" which is $1 \times 10^{-6}$ meter.

As used herein, "Particle Size Distribution (P.S.D)" means the cumulative volume size distribution of equivalent spherical diameters as determined by laser diffraction in Malvern Master Sizer 2000 equipment or its equivalent. "Mean particle size distribution, i.e., $D_{50}$" correspondingly, means the median of said particle size distribution.

By "substantially pure" is meant having purity greater than about 99%, specifically greater than about 99.5%, and more specifically greater than about 99.9% measured by HPLC.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The term wt % refers to percent by weight. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. An amorphous form of imatinib mesylate having a water content of less than 0.5 percent by weight, based on the total weight of the amorphous imatinib mesylate, characterized by a powder X-ray diffraction pattern in accordance with FIG. 1.

2. The amorphous imatinib mesylate of claim 1, having a water content of less than 0.4 percent by weight.

3. The amorphous imatinib mesylate of claim 1, having a water content of less than 0.1 percent by weight.

4. A process for the preparation of amorphous imatinib mesylate having a water content less than 0.5 percent by weight of claim 1, comprising:
   a) forming a first solution of imatinib mesylate in an anhydrous solvent medium comprising a first organic solvent and a second organic solvent, wherein the first organic solvent is selected from the group consisting of $C_1$ to $C_4$ straight or branched chain alcohols, chlorinated hydrocarbons, and mixtures thereof, and wherein the second organic solvent is an aromatic hydrocarbon solvent;
   b) heating the first solution obtained in step-(a) under azeotropic conditions at a temperature of about 35° C. to about 110° C. to form a heated first solution;
   c) removing greater than 50% of the first organic solvent from the heated first solution azeotropically at a temperature of about 35° C. to about 110° C. to form a reaction mass;
   d) heating the reaction mass obtained in step-(c) azeotropically at a temperature of about 110° C. to about 150° C. to form a heated reaction mass;
   e) removing greater than 50% of the remaining organic solvent from the heated reaction mass at a temperature of about 110° C. to about 150° C., optionally under azeotropic conditions, to obtain a residue containing amorphous imatinib mesylate having a water content less than about 0.5 percent by weight, based on the total weight of the amorphous imatinib mesylate;
   (f) dissolving the residue obtained in step-(e) in a third organic solvent selected from the group consisting of $C_1$ to $C_4$ straight or branched chain alcohols, chlorinated hydrocarbon solvents, and mixtures thereof to form a second solution; and
   g) removing greater than 50% of the solvent from the second solution obtained in step-(f) to afford amorphous imatinib mesylate having a water content less than 0.5 percent by weight, based on the total weight of the amorphous imatinib mesylate.

5. The process of claim 4, wherein the first organic solvent used in step-(a) is selected from the group consisting of methanol, ethanol, n-propanol, isopropanol, tert-butanol, n-butanol, methylene chloride, chloroform, and mixtures thereof; and wherein the second organic solvent is selected from the group consisting of toluene, xylene, and mixtures thereof.

6. The process of claim 5, wherein the first organic solvent is selected from the group consisting of methanol, chloroform, and mixtures thereof; and wherein the second organic solvent is toluene.

7. The process of claim 4, wherein the solution obtained in step-(a) or step-(f) is further subjected to carbon treatment.

8. The process of claim 4, wherein the heating in step-(b) is carried out at a temperature of about 100° C. to about 110° C., from about 15 minutes to about 2 hours.

9. The process of claim 4, wherein the removal of solvent in step-(c) is accomplished by azeotropic distillation of the first organic solvent from the solution.

10. The process of claim 9, wherein the distillation is carried out at a temperature of about 100° C. to about 110° C.

11. The process of claim 4, wherein the heating in step-(d) is carried out at a temperature of about 110° C. to about 130° C., from about 30 minutes to about 5 hours.

12. The process of claim 4, wherein the removal of solvent in step-(e) is accomplished by evaporation of the solvent, concentrating the solution or distillation of solvent at a temperature of about 110° C. to about 140° C.

13. The process of claim 4, wherein the third organic solvent used in step-(f) is selected from the group consisting of methanol, ethanol, isopropanol, methylene chloride, chloroform, and mixtures thereof.

14. The process of claim 13, wherein the third organic solvent is selected from the group consisting of methanol, chloroform, and mixtures thereof.

15. The process of claim 4, wherein the removal of the solvent in step-(g) is accomplished by distillation or complete evaporation of the solvent, spray drying, vacuum drying, lyophilization or freeze drying, or a combination thereof.

16. The process of claim 4, wherein the amorphous imatinib mesylate obtained has a purity of about 99% to about 99.99% as measured by high pressure liquid chromatography.

17. A pharmaceutical composition comprising amorphous imatinib mesylate having a water content less than 0.5 percent by weight, based on the total weight of the amorphous imatinib mesylate, and characterized by a powder X-ray diffraction pattern in accordance with FIG. 1, and one or more pharmaceutically acceptable excipients.

18. The pharmaceutical composition of claim 17, wherein the pharmaceutical composition is a solid dosage form or an oral suspension.

19. The pharmaceutical composition of claim 17, wherein the amorphous imatinib mesylate having water content less than 0.5 percent by weight has a $D_{90}$ particle size of less than or equal to 400 microns.

20. The pharmaceutical composition of claim 19, wherein the $D_{90}$ particle size is less than or equal to 200 microns.

\* \* \* \* \*